United States Patent [19]

Lee et al.

[11] Patent Number: 5,451,581
[45] Date of Patent: Sep. 19, 1995

[54] ANTIBIOTIC LL-14E605β AND O-METHYL-LL-14E605β

[76] Inventors: May D. Lee, 19 Shuart R., Monsey, N.Y. 10952; Peter T. Northcote, 35 Riverside Ave., Haverstraw, N.Y. 10927; Mary Lechevalier, R.R. 2, Box 2235, Morrisville, Vt. 05661

[21] Appl. No.: 64,476

[22] Filed: May 21, 1993

[51] Int. Cl.$^6$ .................. C07D 515/22; A61K 31/44; A61K 31/71
[52] U.S. Cl. .................. 514/279; 514/28; 514/183; 210/748; 435/76; 435/119; 435/252.1; 435/822; 536/7.1; 536/16.8; 536/17.3; 536/17.4; 540/456
[58] Field of Search .............. 540/456; 536/16.8, 17.3, 536/17.4, 7.1; 514/28, 183, 279

[56] References Cited
U.S. PATENT DOCUMENTS 4,304,855 12/1981 Sebek et al. .................. 435/75
4,478,831 10/1984 Keller-Juslen .................. 424/181
5,081,024 1/1992 Kuwahara et al. .................. 435/106

FOREIGN PATENT DOCUMENTS 73329 3/1983 European Pat. Off. .
2921148 12/1979 Germany .

OTHER PUBLICATIONS

Depaire, H. et al., Tetrahedron Lett., (1977), No. 16, pp. 1403–1406.

Primary Examiner—Mukund J. Shah
Assistant Examiner—Philip I. Datlow

[57] ABSTRACT

This invention relates to the antibiotics LL-14E605β and O-methyl-LL-14E605β derived from the microorganism *Sebekia benihana* which are useful as antibacterial agents.

4 Claims, 12 Drawing Sheets

LL-14E605β

LL-14E605β

ANTIBIOTIC LL-14E605β AND O-METHYL-LL-14E605β

BACKGROUND OF THE INVENTION

1. Field of the Invention

This invention relates to new antibacterial agents designated LL-14E605β and O-methyl-LL-14E605β, to their production by fermentation, to methods for their recovery and concentration from crude solutions and to processes for their purification. The present invention includes within its scope the antibacterial agents in dilute form, as crude concentrates, as a complex of various or all components, in pure form as individual components and novel strains of Sebekia.

2. Description of the Prior Art

The LL-14E605 antibiotics of this invention are related to but clearly distinguishable from nosiheptide (Depaire, H. et al, Tetrahedron Lett., 1977; Eur. Pat., 73,329, 1983) and antibiotic S-54832A (U.S. Pat. No. 4,478,831, 1984; Ger. Patent 2,921,148, 1979).

BRIEF DESCRIPTION OF THE DRAWINGS

FIG. I is the ultraviolet absorption spectrum of LL-14E605β (3.3 μg/ml solution in methanol);

FIG. II is the infrared absorption spectrum of LL-14E605β (KBr disc);

Figure 1:
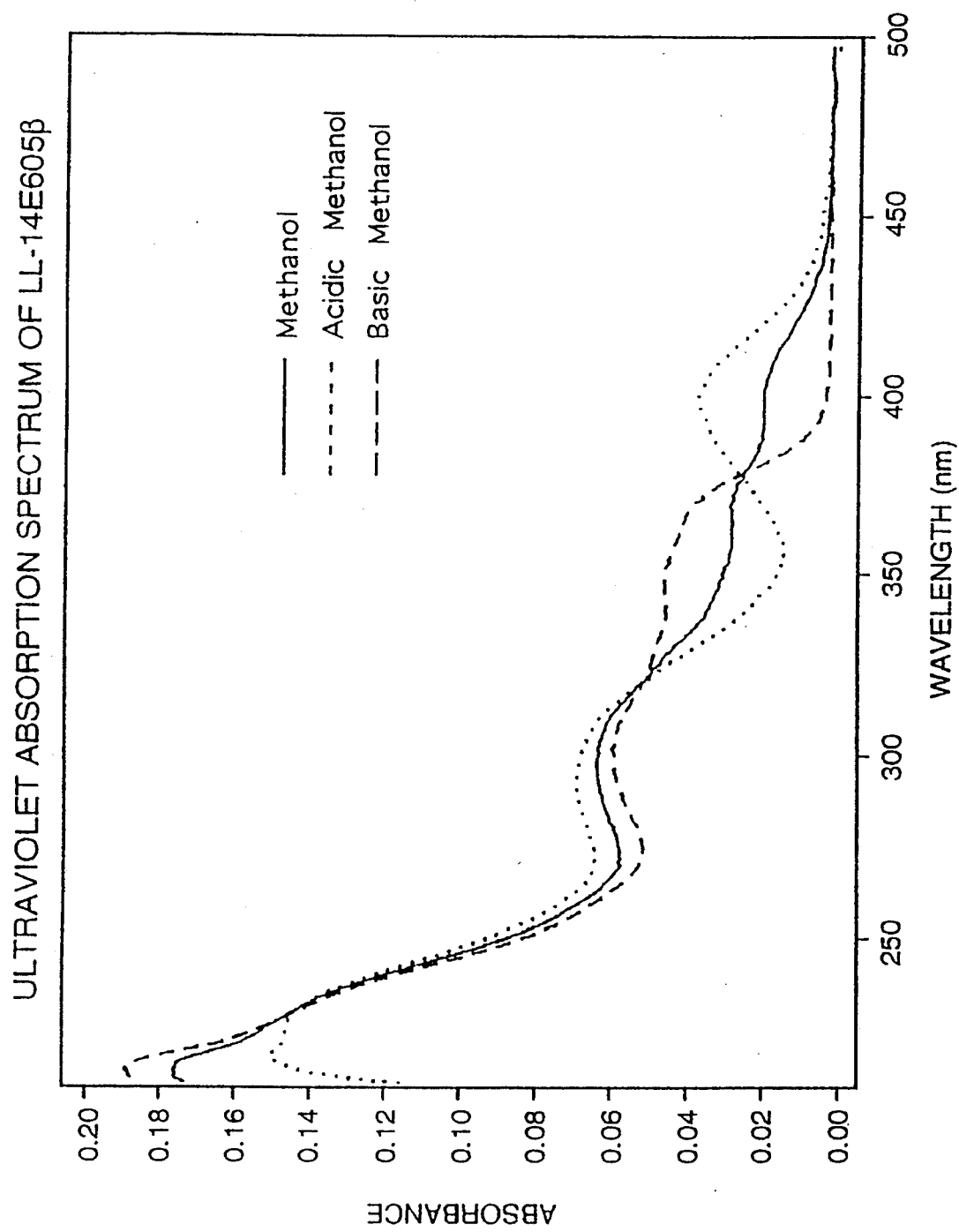
Figure 2:
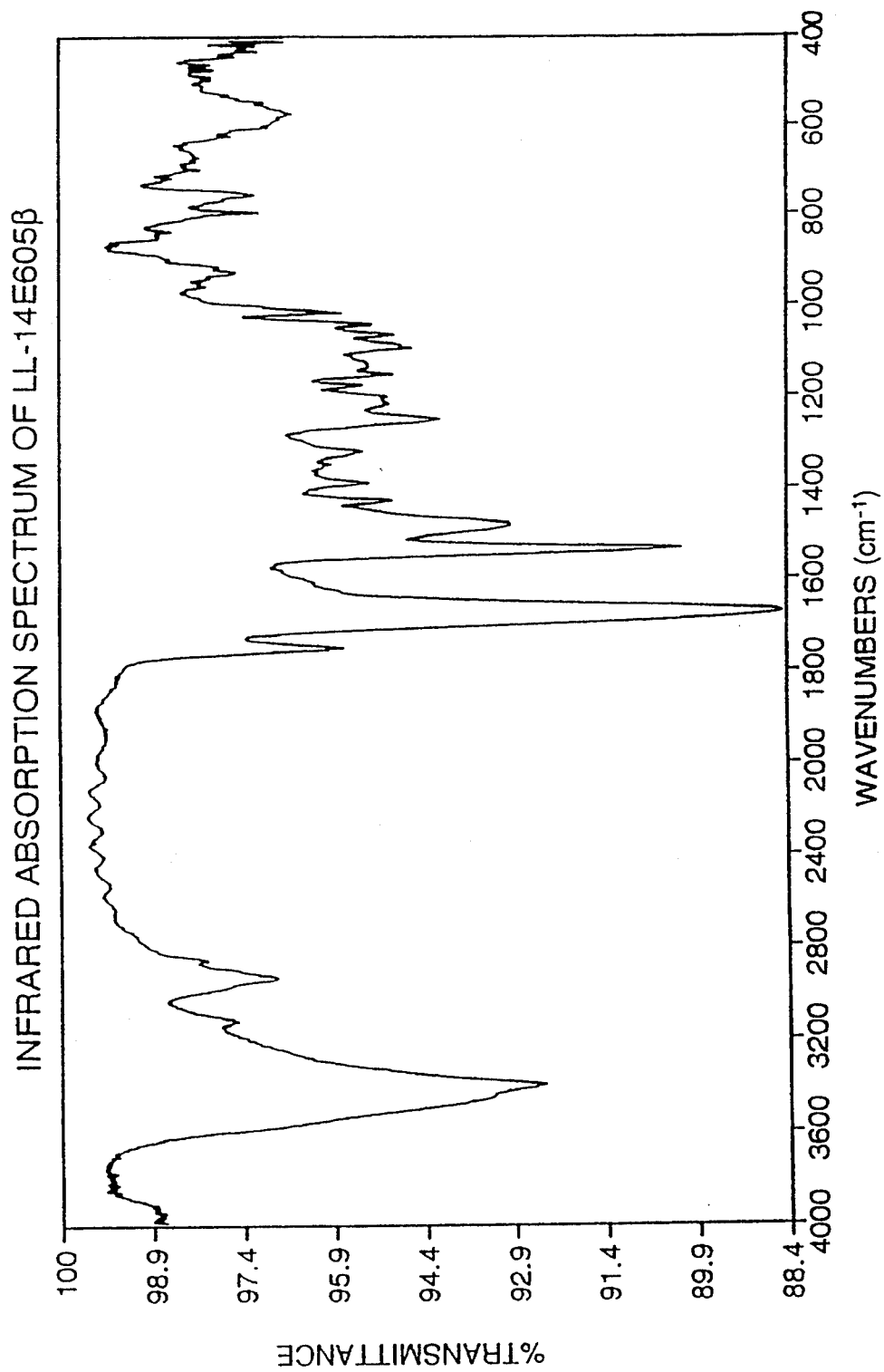
Figure 3:
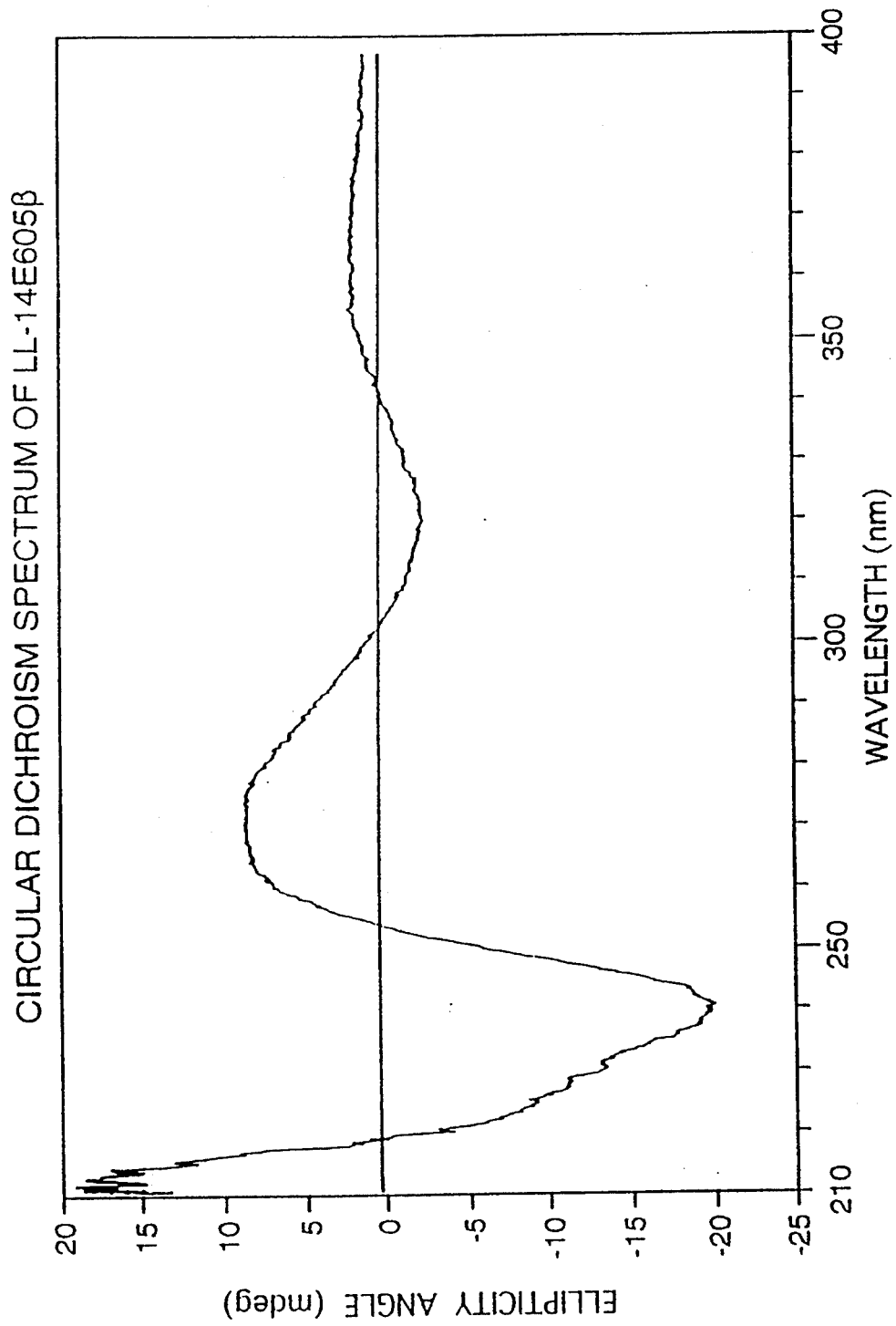
Figure 4:
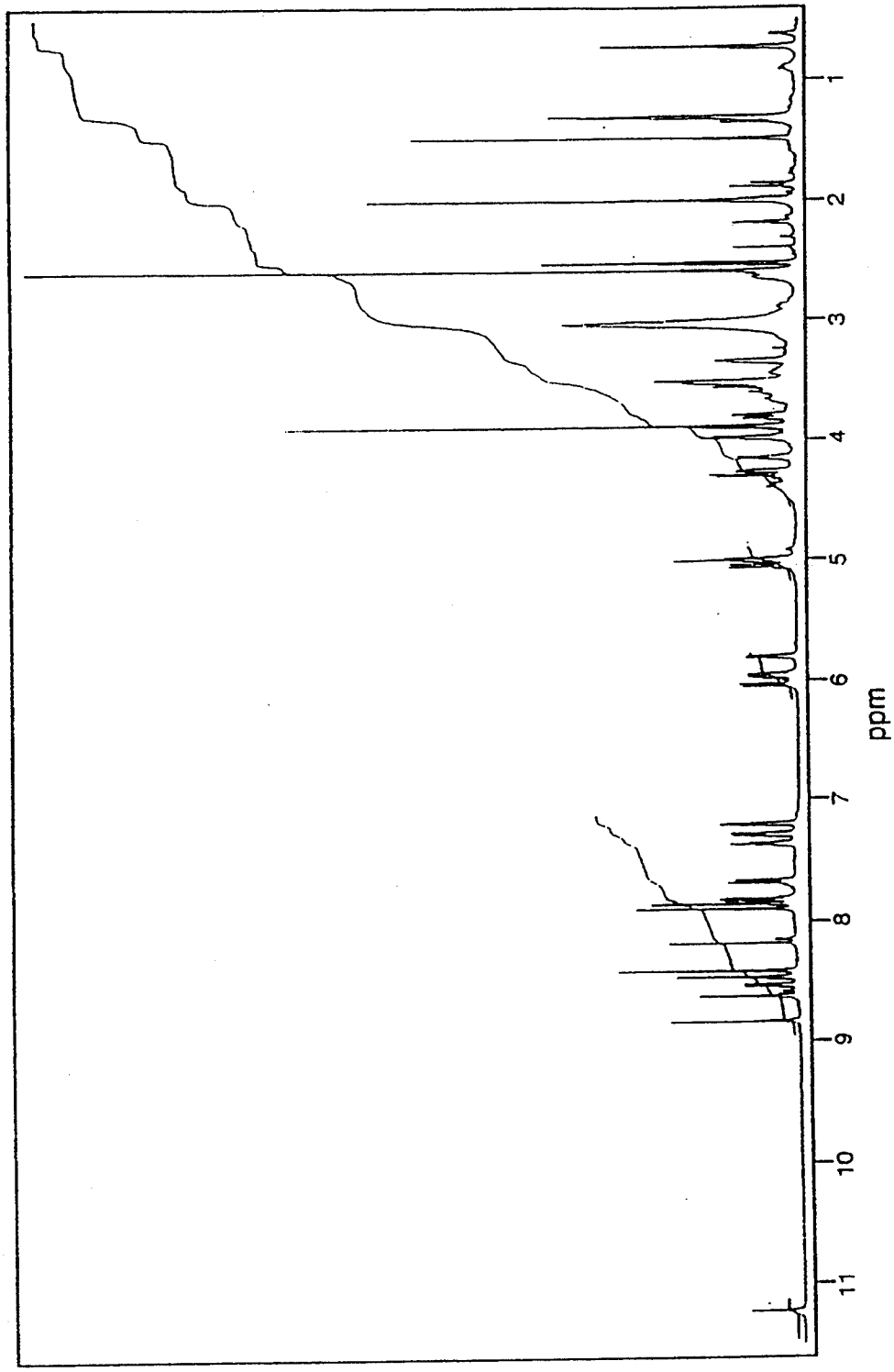
Figure 5:
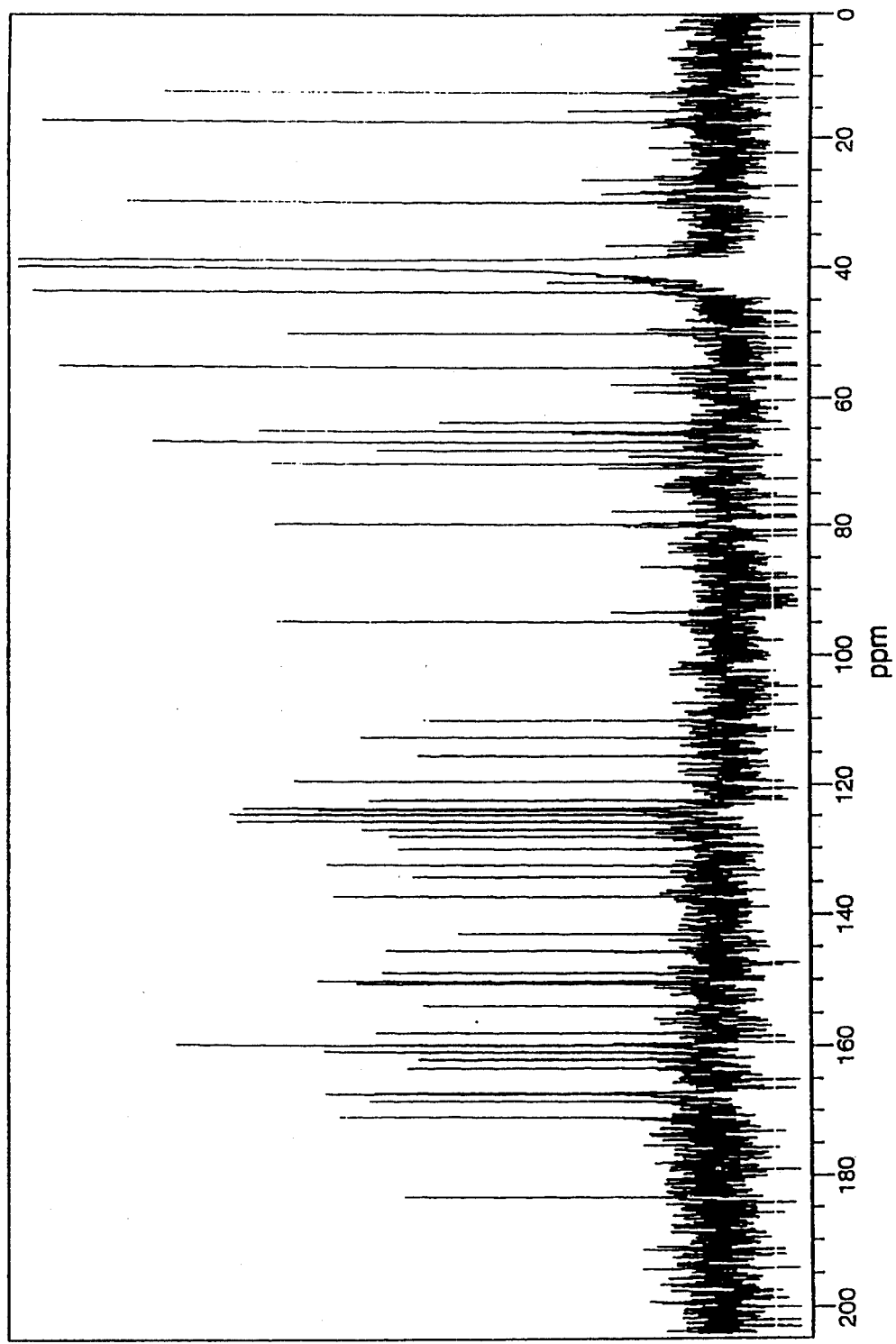
Figure 6:
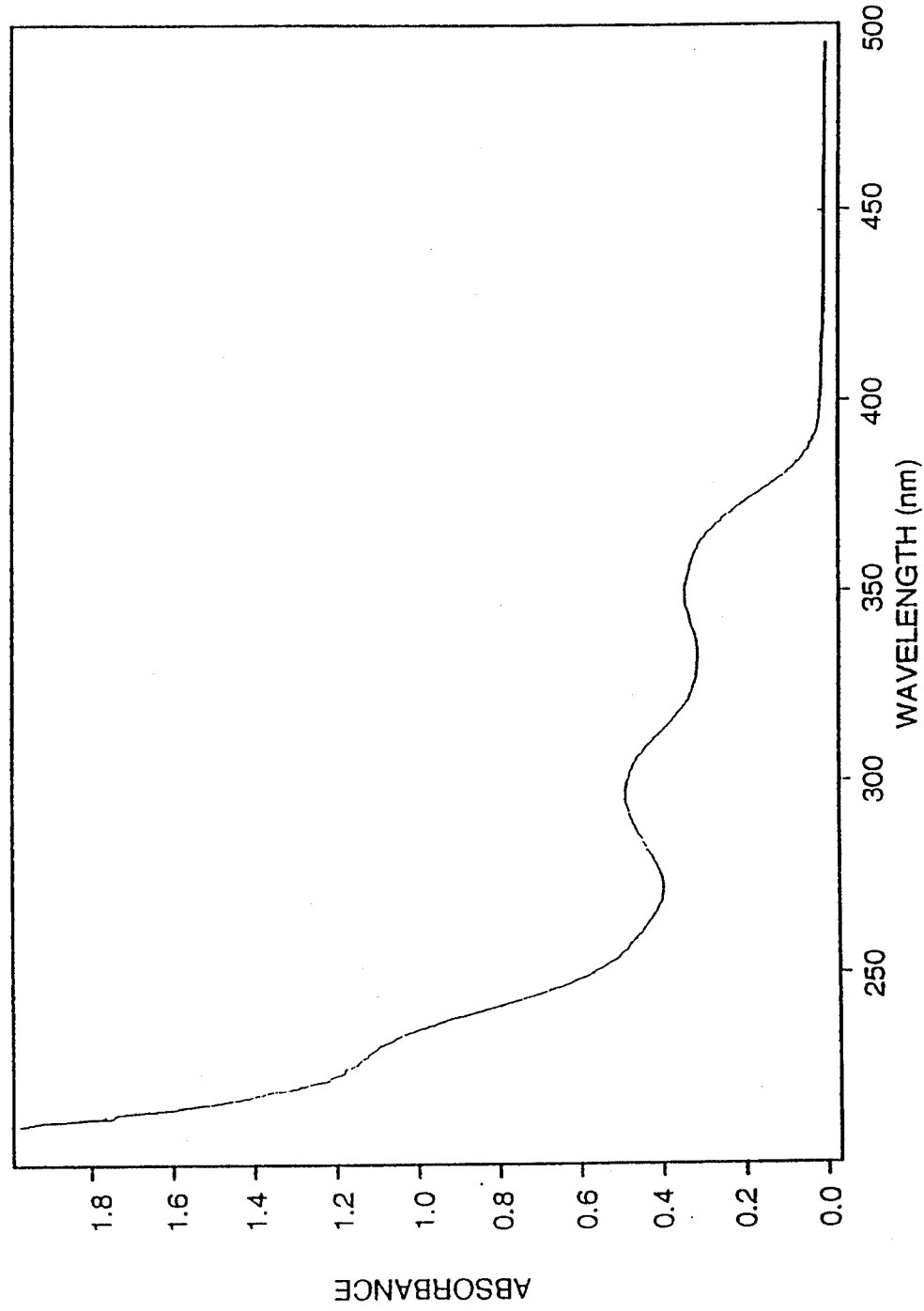
Figure 7:
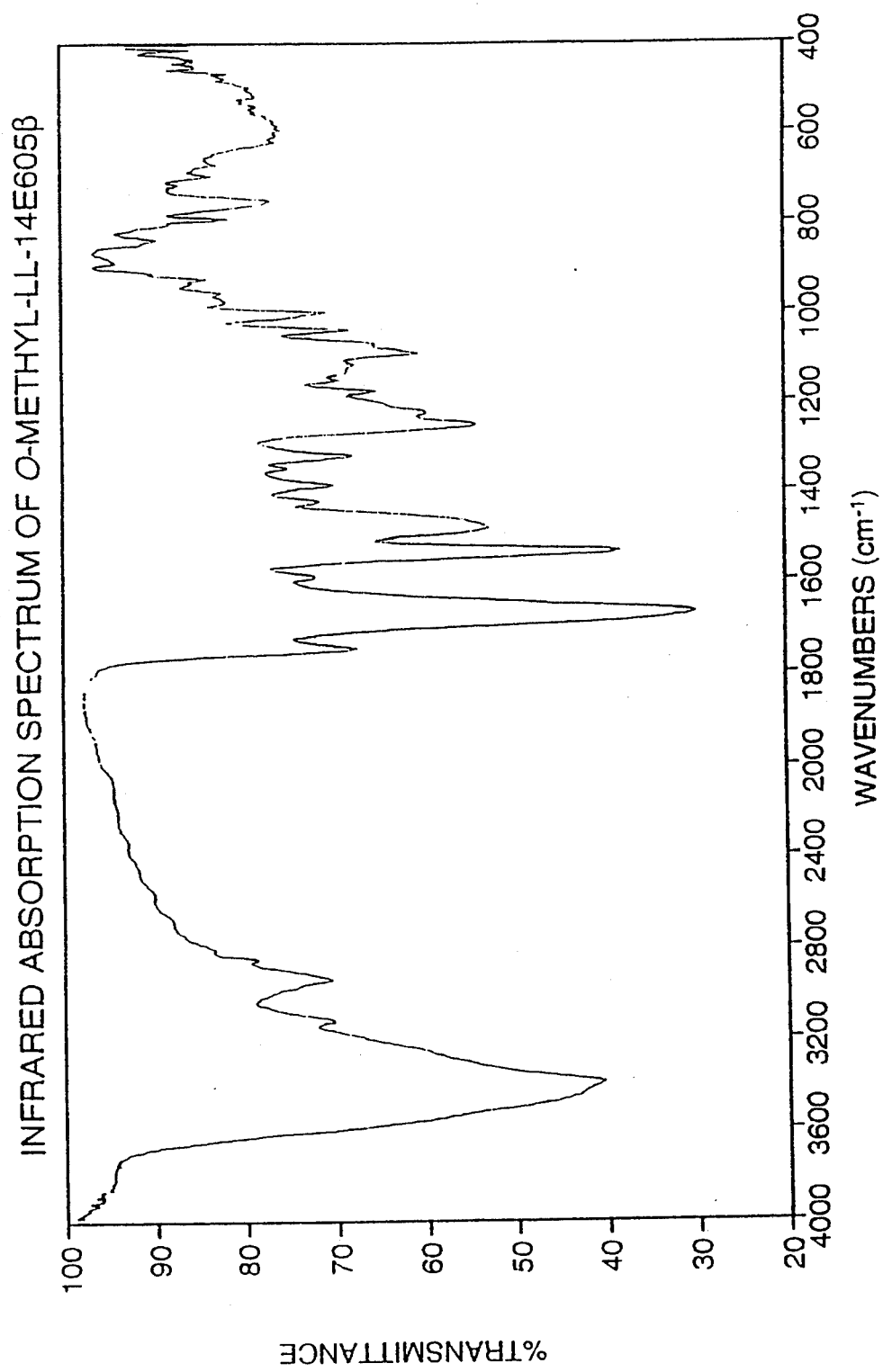
Figure 8:
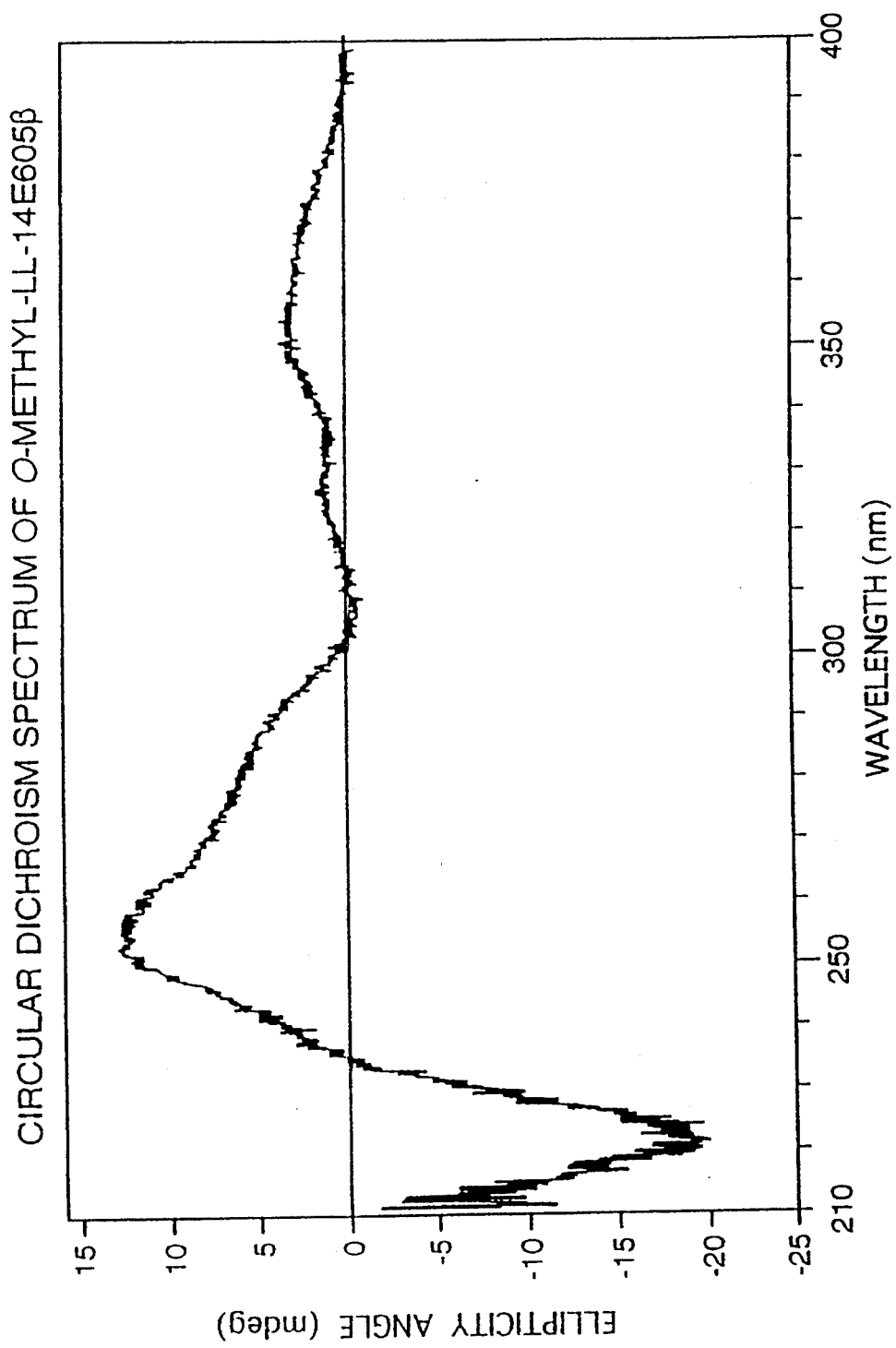
Figure 9:
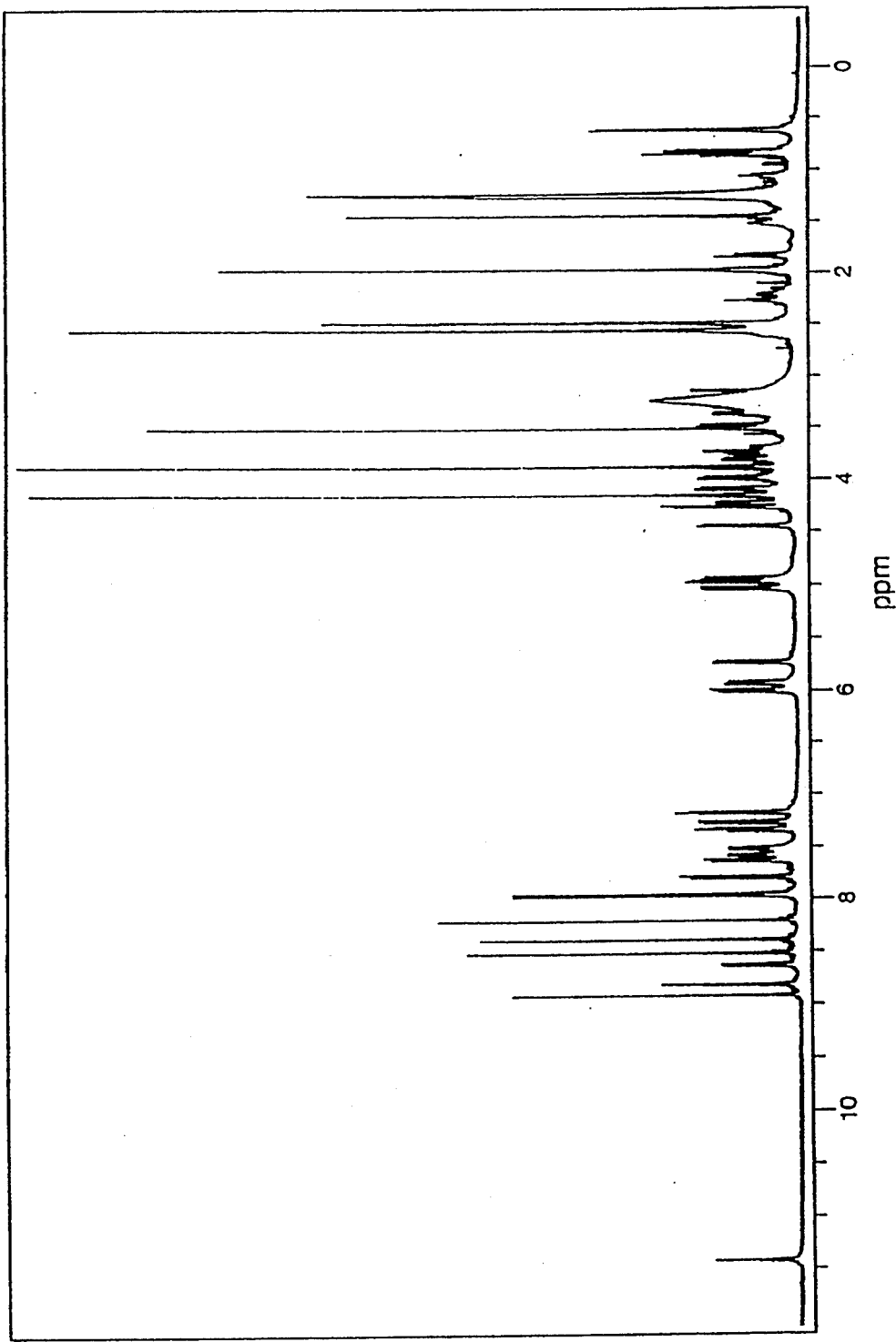
Figure 10:
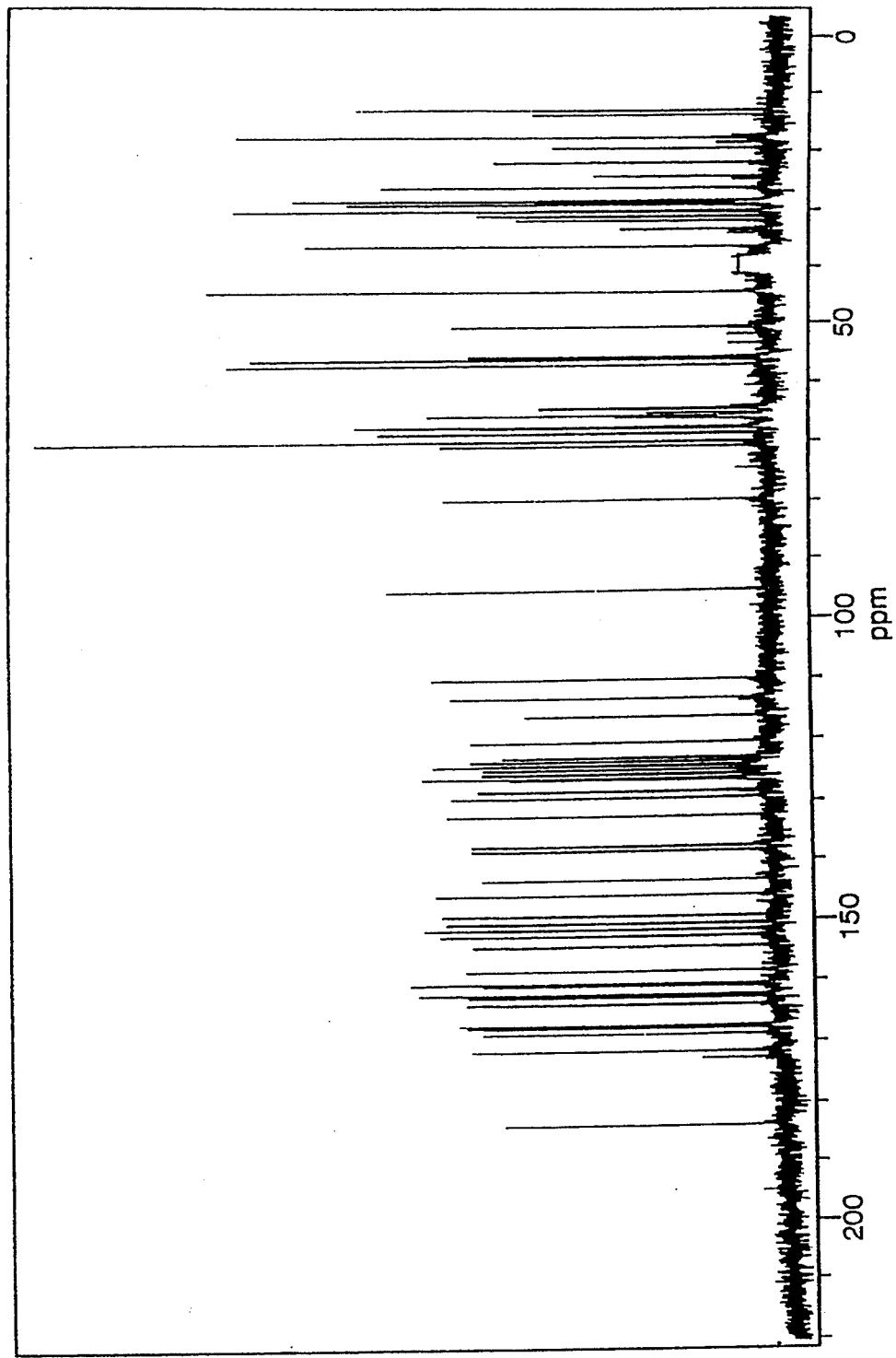
Figure 11:
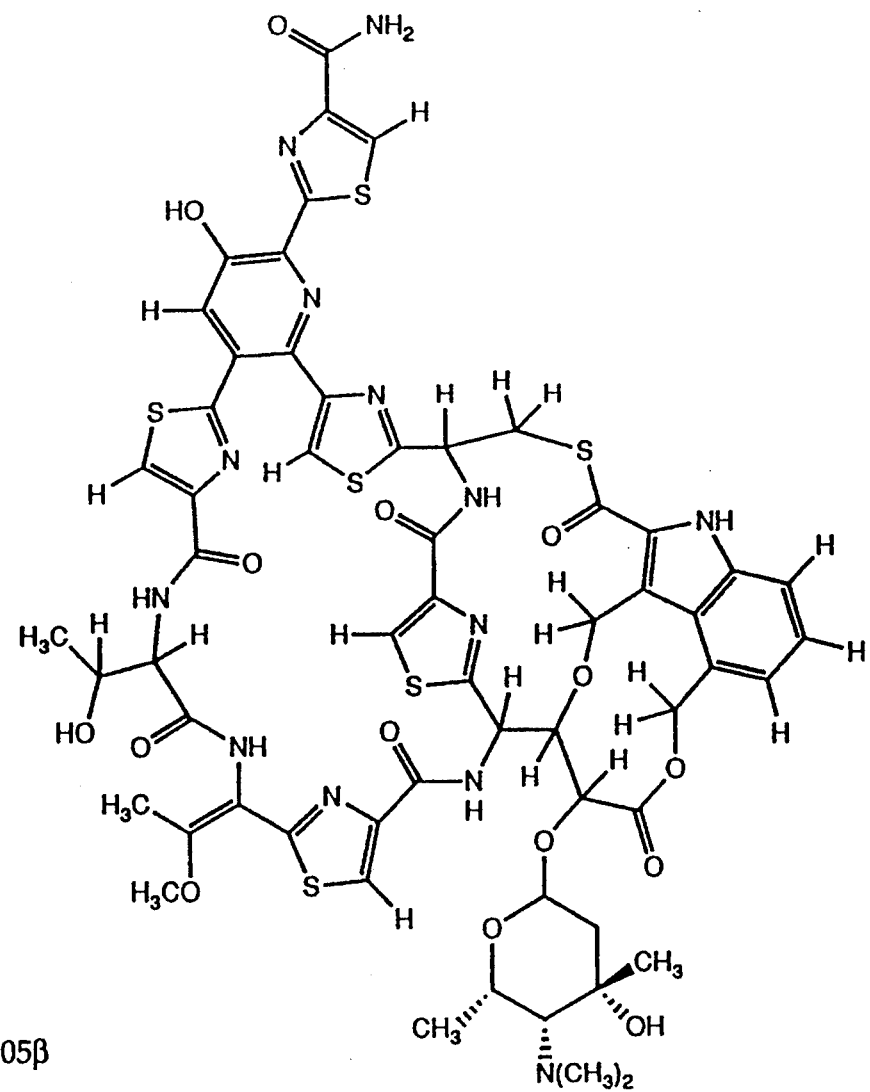
Figure 12:
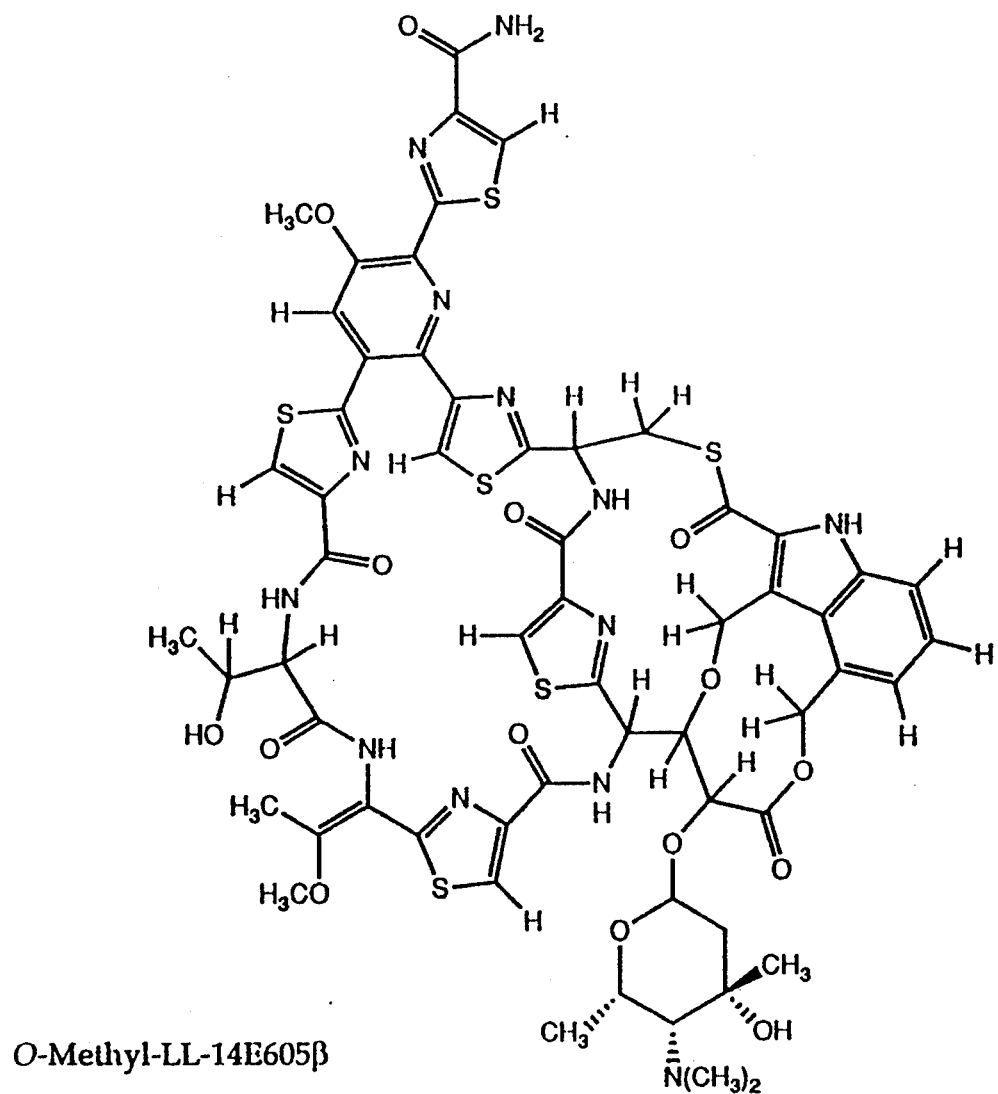

FIG. III is the circular dichroism spectrum of LL-14E605β (10 μg/ml solution in methanol, 20 mm cell);

FIG. IV is the proton magnetic resonance spectrum of LL-14E605β (500 MHz, dimethyl sulfoxide-d$_6$, 50° C.);

FIG. V is the carbon-13 magnetic resonance spectrum of LL-14E605β (500 MHz, dimethyl sulfoxide-d$_6$, 50° C.);

FIG. VI is the ultraviolet absorption spectrum of O-methyl-LL-14E605β (20 μg/ml solution in methanol);

FIG. VII is the infrared absorption spectrum of O-methyl-LL-14E605β (KBr disc);

FIG. VIII is the circular dichroism spectrum of O-methyl-LL-14E605β (20 μg/ml solution in methanol, 10 mm cell);

FIG. IX is the proton magnetic resonance spectrum of O-methyl-LL-14E605β (500 MHz, dimethyl sulfoxide-d$_6$, 50° C.);

FIG. X is the carbon-13 magnetic resonance spectrum of O-methyl-LL-14E605β (500 MHz, dimethyl sulfoxide-d$_6$, 50° C.);

FIG. XI is the chemical structure of LL-14E605β;

FIG. XII is the chemical structure of O-methyl-LL-14E605β;

DETAILED DESCRIPTION OF THE INVENTION

Antibiotic O-methyl-LL14E605β of this invention is an O-methylether of LL-14E605β prepared by reacting LL-14E605β with a methylating agent such as diazomethane. Antibiotic LL-14E605β is the most active component of the LL-14E605 complex and is present in the fermentations of 14E605 (LC40T-67) as a minor component. Its concentration in partially purified LL-14E605 complex could be increased greatly by photolysis at the expense of a less active component which is not characterized in the present invention.

The physico-chemical characteristics of LL-14E605β and its methyl ether, O-methyl-LL-14E600β are described below:

LL-14E605β

1. Molecular weight: 1367 ([M+H]$^+$ at m/e 1367 [±1 amu] is observed by Electrospray MS);
2. Molecular formula: $C_{58}H_{57}N_{13}O_{15}S_6$, exact mass for M+Na is determined by high resolution FAB-MS to be 1390.2307 for $C_{58}H_{57}N_{13}O_{15}S_6Na$;
3. Ultraviolet absorption spectrum: as shown in FIG. I (methanol, acidic methanol, basic methanol) with absorption maxima (nm) and molar extinction coefficients (ε) as listed below:

| MeOH, nm (E): | 302 nm (27,000) | 370 nm (11,900) | 400 nm (8400) |
|---|---|---|---|
| 5 mN HCl in MeOH, nm (E): | 302 nm (24,900) | 352 nm (19,200) | 370 nm (16,000) |
| 5 mM NaOH in MeOH, nm (E): | 295 nm (28,800) | 400 nm (15,300) | |

4. Infrared absorption spectrum: as shown in FIG. II (KBr disc);
5. Circular dichroism spectrum: as shown in FIG. III (methanol solution) with the following maxima (nm) and minima (nm) and molar ellipticity (Θ): 240 nm (−13,850); 271 nm (+57,300); 319 nm (−19,000);
6. Proton magnetic resonance spectrum: as shown in FIG. IV (500 MHz, dimethyl sulfoxide-d$_6$, 50° C., referenced to DMSO center line, 2.49 ppm);
7. Carbon-13 magnetic resonance spectrum: as shown in FIG. V (500 MHz, dimethyl sulfoxide-d$_6$, 50° C., referenced to DMSO centerline, 39.50 ppm) with significant peaks and their assignments as listed below:

| | | | |
|---|---|---|---|
| 12.71 (CH$_3$) | 67.22 (CH$_2$) | 126.23 (CH) | 158.14 (C) |
| 17.51 (CH$_3$) | 67.26 (C) | 126.23 (CH) | 160.16 (C) |
| 17.61 (CH$_3$) | 68.24 (CH) | 127.18 (CH) | 160.27 (C) |
| 30.05 (CH$_3$) | 70.44 (CH) | 128.23 (C) | 160.52 (C) |
| 30.15 (CH$_3$) | 79.82 (CH) | 130.19 (C) | 161.27 (C) |
| 40.21 (CH$_3$) | 94.91 (CH) | 132.50 (C) | 162.39 (C) |
| 44.04 (CH$_3$) | 109.94 (C) | 134.24 (C) | 163.54 (C) |
| 44.04 (CH$_3$) | 112.93 (C) | 137.36 (C) | 167.25 (C) |
| 50.17 (CH) | 115.93 (CH) | 142.90 (C) | 167.60 (C) |
| 50.30 (CH) | 119.94 (CH) | 145.56 (C) | 167.64 (C) |
| 55.25 (CH) | 122.73 (CH) | 148.89 (C) | 168.67 (C) |
| 55.69 (CH$_3$) | 123.96 (CH) | 150.17 (C) | 171.35 (C) |
| 64.11 (CH$_2$) | 124.18 (C) | 150.49 (C) | 183.73 (C) |
| 65.38 (CH) | 124.63 (CH) | 150.75 (C) | |
| 66.09 (CH) | 125.28 (CH) | 154.05 (C) | |

O-methyl-LL14E605β

1. Molecular weight: 1381, calculated from molecular formula;
2. Molecular formula: $C_{59}H_{59}N_{13}O_{15}S_6$, exact mass for M+Na is determined by high resolution FAB-MS to be 1404.2474 for $C_{59}H_{59}N_{13}O_{15}S_6Na$;
3. Ultraviolet absorption spectrum: as shown in FIG. VI (methanol solution) with the following absorption maxima (nm) and molar extinction coefficients (ε): 296 nm (33,200); 349 nm (23,800), no significant shift in acidic or basic methanol;
4. Infrared absorption spectrum: as shown in FIG. VII (KBr disc);
5. Circular dichroism spectrum: as shown in FIG. VIII (methanol solution) with the following maxima (nm) and minima (nm) and molar ellipicity (Θ): 221 nm (−127,500); 255 nm (+85,000); 326 nm (+10,000); 354 nm (+22,500);

6. Proton magnetic resonance spectrum: as shown in FIG. IX (500 MHz, dimethyl sulfoxide-$d_6$, 50° C., referenced to DMSO center line, 2.49 ppm);

7. Carbon-13 magnetic resonance spectrum: as shown in FIG X (500 MHz, dimethyl sulfoxide-$d_6$, 50° C. referenced to DMSO center line 39.50 ppm) with significant peaks and their assignments as listed below:

| | | | |
|---|---|---|---|
| 12.79 (CH$_3$) | 65.62 (CH) | 124.83 (CH) | 154.11 (C) |
| 17.54 (CH$_3$) | 67.06 (C) | 125.44 (CH) | 158.22 (C) |
| 17.60 (CH$_3$) | 67.32 (CH$_2$) | 126.19 (CH) | 160.22 (C) |
| 30.07 (CH$_2$) | 68.30 (CH) | 126.47 (CH) | 160.36 (C) |
| 30.20 (CH$_3$) | 70.54 (CH) | 128.59 (C) | 160.72 (C) |
| 39.95 (CH$_2$) | 79.81 (CH) | 129.40 (C) | 162.12 (C) |
| 44.14 (CH$_3$) | 94.89 (CH) | 132.91 (C) | 162.50 (C) |
| 44.14 (CH$_3$) | 109.87 (C) | 137.42 (C) | 163.76 (C) |
| 50.23 (CH) | 112.96 (C) | 138.27 (C) | 163.84 (C) |
| 50.36 (CH) | 116.05 (CH) | 143.09 (C) | 167.29 (C) |
| 55.31 (CH) | 120.27 (CH) | 145.54 (C) | 167.62 (C) |
| 55.79 (CH$_3$) | 122.78 (CH) | 148.92 (C) | 168.66 (C) |
| 56.72 (CH$_3$) | 123.39 (CH) | 150.14 (C) | 171.40 (C) |
| 64.15 (CH$_2$) | 124.01 (CH) | 151.23 (C) | 183.80 (C) |
| 65.28 (CH) | 124.24 (C) | 152.28 (C) | |

The chemical structures of LL-14E605β and O-methyl-LL-14E605β with the relative stereochemistry of the glycoside are disclosed in FIGS. XI and XII.

The preferred analytical separation of LL-14E605β and O-methyl-LL-14E605β uses the following conditions:

Column: PLRP-S®, 5 μm, 100 A, 150×4.6 nm (Phenomenex).
Solvent: Acetonitrile—0.1M Trifluoroacetic acid adjusted to pH 2.0 with NH$_4$OH (45/55)
Flow rate: 1.0 ml.min.
Detection: UV absorbance at 350 nm
Sample: 10 μl of a 1.0 mg/ml solution in MeOH—CH$_2$Cl$_2$ (80/20)
Retention: LL-14E605β, 3.9 minutes;
O-methyl-LL-14E605β, 3.2 min.

The new antibacterial agent LL-14E605β is formed during the cultivation under controlled conditions of a new strain of Sebekia.

This microorganism is maintained in the culture collection of the Medical Research Division, American Cyanamid Company, Pearl River, N.Y. 10965 as culture number 14E605. A viable culture of this new microorganism has been deposited on Apr. 14, 1993 under conditions of the Budapest Treaty with the Patent Culture Collection Laboratory, Northern Regional Research Center, U.S. Department of Agriculture, Peoria, Ill. 61604, and has been added to its permanent collection. It has been assigned the strain designation NRRL 21083 by said depository.

Culture 14E605 is a new strain of Sebekia isolated from the rhizosphere of a white mulberry tree growing in El Khanka, Egypt. Based on the physiological data (Table III), culture 14E605 is considered either a new subspecies of *Sebekia benihana* or a new species of Sebekia.

Culture 14E605 has the following cultural, macromorphological and physiological characteristics described in Tables I, II and III, respectively.

TABLE I

| | Cultural Characteristics | |
|---|---|---|
| Characteristic | LL-14E605 | *Sebekia benihana*[b] |
| Aerial Mycelium | Short Spore Chains | Short Spore Chains |
| Fragmentation of Substrate Mycelium | None | None |
| Zoospores and Sporangia | Pseudosporangia | Pseudosporangia |
| Spore Chain | ≦10 | ≦10 |
| Spore Shape | — | — |
| Spore Surface | — | Smooth and Spring |
| Temperature Growth | <45° C. | <45° C. |
| Salt Tolerance | <5% | <5% |
| DAP Analysis | meso: L-DAP (3:1) | meso: L-DAP (5:1) |
| Whole Cell Sugars | Ribose, Mannose, Madurose, Galactose | Madurose and Mannose |

TABLE II

| | Macromorphology | |
|---|---|---|
| Medium | LL-14E605 Morphology[a] | *Sebekia benihana* Morphology[ab] |
| Yeast-MaLt (ISP2) | G: Abundant<br>AM: White to Light Gray (263,264)<br>SM: Dark Olive Brown (96)<br>SP: Light Brown | G: Abundant<br>AM: Pink Gray to Light Gray (10,264)<br>SM: Dark Red Brown (44)<br>SP: Brown |
| Oatmeal (ISP3) | G: Abundant<br>AM: None<br>SM: Gray Yellow to Dark Gray Yellow (90,91)<br>SP: Light Brown | G: Abundant<br>AM: Bright Pink (33)<br>SM: Light Yellow Brown to Slight Red Brown (76,40)<br>SP: Light Brown |
| Inorganic Salts-Starch (ISP4) | G: Abundant<br>AM: Pale Yellow Green (121)<br>SM: Pale Green Yellow (104)<br>SP: None | G: Abundant<br>AM: Pale Yellow (89)<br>SM: Yellow white to pale Yellow (92,89)<br>SP: None |
| Glycerol-Asparagine (ISP5) | G: Sparse<br>AM: White (263)<br>SM: Clear<br>SP: None | G: Sparse<br>AM: Pale YeLlow Pink to Yellow White (31,92)<br>SM: Clear<br>SP: None |

G, growth; AM, aerial mycelium; SM, substrate mycelium; SP, soluble pigment
[a]ISCC, NationaL Bureau of Standard Centroid color Charts, Publication 440, Washington, D.C., 1976.
b = culture number NRRL 11,111.

TABLE III

| | Physiological Reactions | |
|---|---|---|
| | LL-14E605 | *Sebekia benihana* |
| Utilization of Carbon Sources: | | |
| D-Glucose | ± | + |
| L-Arabinose | − | + |
| Sucrose | − | − |
| D-Xylose | − | + |
| I-Inositol | − | + |
| D-Mannitol | − | − |
| beta-D-Fructose | ± | + |
| a-L-Rhamnose | ± | + |
| Raffinose | + | − |
| Cellulose | − | − |
| Hydrolysis of: | | |
| Casein | + | + |
| Xanthine | − | − |
| Hypoxanthine | + | ± |
| Tyrosine | ± | + |
| Adenine | − (NG) | + |
| Esculin | + | + |

TABLE III-continued

| Physiological Reactions | LL-14E605 | Sebekia benihana |
|---|---|---|
| Production of: | | |
| Urease | − | − |
| Melanin | − | − |
| Decarboxylation of: | | |
| Acetate | + | + |
| Benzoate | − | − |
| Citrate | − | − |
| Lactate | + | + |
| Malate | ± | + |
| Mucate | ± | − |
| Oxalate | − | − |
| Propionate | − | − |
| Pyruvate | + | + |
| Succinate | + | + |
| Tartrate | − | − |
| Acid Production from: | | |
| Arabinose | + | + |
| Dulcitol | − | − |
| Erythritol | − | − |
| Glucose | + | + |
| Inositol | − | + |
| Lactose | + | − |
| Mannitol | + | − |
| Mannose | + | + |
| Methyl-a-D-glucoside | + | − |
| Melibiose | − | + |
| Raffinose | + | − |
| a-L-Rhamnose | + | + |
| Sorbitol | + | − |
| Trehalose | + | + |

+: positive, −: negative, ±: weak

The in vitro antibacterial activity of LL-14E605β and O-methyl-LL-14E605β is determined against a spectrum of gram positive and gram-negative bacteria by a standard agar dilution method. Mueller-Hinton agar containing two fold decreasing concentrations of the antibiotics is poured into petri plates. The agar surfaces are inoculated with 1 to $5 \times 10^4$ colony forming units of bacteria by means of a Steer's replicating device. The lowest concentration of the LL-14E605 antibiotics that inhibits growth of a bacterial strain after about 18 hours of incubation at approximately 35° C. is recorded as the minimal inhibitory concentration (MIC) for that strain. The results are summarized in Table IV.

TABLE IV

In Vitro Antibacterial Activity of LL-14E605 Antibiotics

| | Minimal Inhibitory Concentrations MIC (mcg/ml) | |
|---|---|---|
| | LL-14E605-beta | O-methyl-L-14E605beta |
| Staphylococcus aureus (NEMC-89-4) | 0.015 | 0.5 |
| Staphylococcus aureus (ID-2371) | 0.015 | 0.5 |
| Staphylococcus aureus (ID-2727) | 0.008 | 0.25 |
| Staphylococcus aureus (SMITH) | 0.008 | 0.25 |
| Staphylococcus aureus (ID-3105) | 0.015 | 0.25 |
| Staphylococcus aureus (4379) | 0.015 | 0.25 |
| Staphylococcus aureus (ATCC 29213) | 0.015 | 0.25 |
| Staphylococcus hemolyticus (ID 4061) | 0.03 | 1 |
| Staphylococcus, coagluase negative (ID-3135) | 0.03 | 1 |
| Staphylococcus, coagluase negative (ID-3276) | 0.008 | 0.5 |
| Staphylococcus, coagluase negative (ID-3120) | 0.06 | 1 |
| Staphylococcus, coagluase negative (ID-3941) | 0.06 | 4 |
| Staphylococcus, coagiuase negative (ID-4615) | 0.015 | 0.25 |
| Enterococcus faecalis (ID-4168) | 0.015 | 8 |
| Enterococcus faecalis (ID-1829) | 0.002 | 8 |
| Enterococcus faecalis (ID-2131) | 0.015 | 4 |
| Enterococcus faecalis (12201) | 0.015 | 4 |
| Enterococcus faecalis (ATCC 29212) | 0.015 | 8 |
| Enterococcus faecium (12202) | 0.004 | 8 |
| Enterococcus faecium (ID-3301) | 0.015 | 8 |
| Enterococcus faecium (ID-4133) | ≦0.005 | 8 |
| Enterococcus avium (ID-3953) | 0.002 | 8 |
| Pseudomanas aeruginosa (ATCC 27853) | >64 | >32 |
| Morganella morganii (VGH 84-11) | >64 | >32 |
| Escherichia coli (J2175) | >64 | >32 |
| Escherichia coli (J2445) | 0.06 | >32 |
| Escherichia coli (ATCC 25922) | >64 | >32 |
| Bacillus cereus (Bacto) | 0.06 | 0.5 |
| Micrococcus luteus (ATCC 9341) | 0.002 | 0.5 |

The in vivo activity of antibiotic LL-14E605β is assessed in female mice, strain CD-1, weighing 20±2 g each, infected intraperitoneally with sufficient Staphylococcus aureus Smith cells suspended in broth to kill approximately 95% to 100% of untreated mice within about 48 hours. Partially purified LL-14E605 complex, containing approximately 3% LL-14E605β, prepared as described in Example 3, is administered subcutaneously at the designated time and dose before and after the infection. The results are summarized in Table V.

TABLE V

| | Dose | |
|---|---|---|
| Level (mg/Kg) | Schedule | #Survived/#Tested |
| 16 | 4, 3, 2, & 1 hour | 4/5 |
| 8 | before & 30 minutes | 3/5 |
| 4 | after infection | 1/5 |
| 2 | | 0/5 |
| 16 | 3, 2, & 1 hour | 4/5 |
| 8 | before & 30 minutes | 0/5 |
| 4 | after infection | 0/5 |
| 2 | | 0/5 |
| 16 | 2 & 1 hour before | 2/5 |
| 8 | & 30 minutes | 0/5 |
| 4 | after infection | 0/5 |
| 2 | | 0/5 |
| 16 | 30 minutes after | 0/5 |
| 8 | infection | 0/5 |
| 4 | | 0/5 |

TABLE V-continued

| Level (mg/Kg) | Dose Schedule | #Survived/#Tested |
|---|---|---|
| 2 | | 0/5 |

When the compounds are employed as pharmaceutical compositions for the treatment of bacterial infections, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions. In all cases, the form must be sterile and must be fluid to the extent that easy syringability exits. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

General Fermentation Conditions

Cultivation of Sebekia 14E605 may be carried out in a wide variety of liquid culture media. In general, media which are useful for the production of these novel antibacterial agents contain assimilable sources of carbon, such as starch, sugar, molasses, glycerol, etc.; assimilable sources of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc. are supplied as impurities of other constituents of the media. Aeration in fermenters and flasks is supplied by forcing sterile air through or onto the surface of the agitated fermenting medium. Further agitation in fermenters is provided by a mechanical impeller. An anti-foaming agent such as silicone may be added as needed.

Fermentations are monitored daily for the production of the LL-14E605 antibiotics by anti microbial assay and are harvested when the expected antimicrobial activity is reached.

General Procedure for the Isolation and Separation of LL-14E605β

Most of the LL-14E605 antibiotics present in the fermentation of 14E605 is associated with the cell mass and can be extracted from the mycelial cake by an organic solvent such as acetone or mixtures of methanol and dichloromethane. The portion of the antibiotics found in the fermentation filtrate can be adsorbed onto a polymeric resin such as Diaion ® HP-20 (Mitsubishi Chemical Industries Ltd.) and recovered by eluting the resin with an organic solvent such as acetone or mixtures of methanol and dichloromethane. Alternatively, the whole fermentation mash can be processed through a tangential flow filtration system equipped with porous ceramic filter elements such as the Ceraflo ® Process System (Millipore). The antibiotics concentrated in the retentate can be extracted efficiently into an organic solvent such as a mixture of methanol and dichloromethane. The crude antibiotic complex can be further purified, before column chromatography, by partition between the upper and lower phases of ternary solvent systems containing water, methanol and dichloromethane and by trituration with water and/or hexane. Further purification of the antibiotic complex can be accomplished by chromatography using adsorbents such as Sephadex ® (LH-20), or alkyl amine bonded silica (Sepralyte ® Primary/Secondary Amine) or polymeric adsorbent (Amberchrom ® CG-161, TosoHaas) to give partially purified LL-14E605 complex. The various antibiotic components in the complex can be converted to the most active component, LL-14E605β, by photolysis. Further purification of LL-14E605 can be achieved by counter current chromatography such as Centrifugal Partition Chromatography or column chromatography using polymeric adsorbent such as Amberchrom® CG-161.

Example 1

Production of the LL-14E605 Complex in 410-L Fermenters

The media used for growing the different stages of the inoculum and for the product of the LL-14E605 complex are identical. It is prepared according to the following formula and sterilized.

| Inoculum and Production Medium | |
|---|---|
| glucose | 10.0 grams/liter |
| dextrin | 20.0 grams/liter |
| yeast extract | 5.0 grams/liter |
| N-Z amine type ® A[1] | 5.0 grams/liter |
| CACO$_3$ (Mississippi Lime) | 1.0 grams/liter |
| FD82 silicone antifoam | 3.0 ml/liter |
| no pH adjustment | |

[1][A pancreatic digest of casein registered trademark of Sheffield Chemical, Norwich, NY]

A 500 ml flask containing 100 ml of the sterilized medium is inoculated with 1 ml of the frozen mycelia of the culture 14E605 (LC40T-67) preserved in 20% glycerol. The flask is incubated on a rotary shaker (210 rpm) at 28° C. for 48 hours to give the S1 inoulum. The S1 inoculum is inoculated into 6 liters of the sterlized medium in a 10-L fermenter. The mixture is incubated at 28° C. with 6 lpm (liters per minute) aeration and 450 rpm agitation for 48 hours to give the S2 inoculum.

The S2 inoculum (6 liters) is inoculated into 290 liters of the sterilized medium in a 410-L fermenter. The fermentation is allowed to proceed at 28° C. with 250 lpm aeration and 250 rpm agitation. The fermentation mash is harvested after 99 hours.

Example 2

Production of the LL-14E605 Complex in 3000-L Fermenters

The same medium as in Example 1 is used. An S2 (10 liters) inoculum prepared as in Example 1 is inoculated into 300 liters of the sterilized medium in a 410-L fermenter. The mixture is incubated at 28° C. with 200 lpm aeration and 200 rpm agitation for 48 hours to give the S3 inoculum. The S3 inoculum (150 liters) is inoculated into 3000 liters of the sterilized medium and the fermentation is allowed to proceed at 28° C. with 2000 lpm aeration and 110 rpm agitation. The fermentation mash is harvested after 100 hours.

Example 3

Recovery of the LL-14E605 Complex from the Mycelium

The harvested fermentation mash (750 liters) prepared as described in Example 1 is stirred with 7.5 liters of toluene. Diatomaceous earth, (16 Kg) is added to the mash mixture and it is filtered. The diatomaceous earth cake is thoroughly mixed with 375 liters of acetone-water (90/10, v/v) and filtered. The filtrate is concentrated and freeze-dried to give 615 g of solid which is partitioned between 60 liters each of water and ethyl acetate. The organic phase is concentrated, dried over anhydrous sodium sulfate and precipitated by addition of hexanes. Work up of the precipitate gives 11.5 g of crude LL-14E605 complex which is further purified by column chromatography on Sephadex® LH-20 as described below. A 500 mg portion of the crude LL-14E605 complex is dissolved in 3 ml of dichloromethane/methanol (80/20) and top-loaded onto a Sephadex® LH-20 (Pharmacia Fine Chemicals) column (1.5×90 cm) packed and equilibrated with the same solvent mixture. The column is eluted at 2 ml/minute with the same solvent mixture and 20 ml fractions are collected. The fractions are analyzed by antimicrobial assay and those active (fractions 4–8) from three such column chromatographic separations are combined and concentrated to give 914 mg of partially purified LL-14E605 complex.

Example 4

Recovery of the LL-14E605 Complex via Diaion® HP-20

The harvested fermentation mash (3900 liters) prepared as described in Example 2 is stirred with 39 liters of toluene. The mixture is adjusted to pH 4.0 with concentrated hydrochloric acid and 780 liters of acetone is added. The mixture is stirred vigorously for four hours and is filtered through diatomaceous earth (115 Kg).

The filtrate (4300 liters) is passed through a Diaion® HP-20 (Mitsubishi Chemical Industries Ltd., 300-L) at 2–3 liter/minute. After washing with 600 liters of water, the column is eluted sequentially with 600 liters each of methanol and 0.6% ammonium hydroxide in methanol (2 parts 30% ammonium hydroxide, 100 parts methanol). Fractions (150 liters each) are collected during the elution and analyzed by antimicrobial assay. Fraction 5 (40% acetone eluate) to 22 (methanol eluate) are pooled and concentrated to dryness in five equal portions. Each portion is triturated with 15 liters of 0.6% ammonium hydroxide in methanol and filtered. The basic methanol solutions are combined and concentrated to a solid residue which is triturated with 30 liters of water and the insoluble solids are collected by centrifugation. Work up of the solids affords 33 grams of crude LL-14E605 complex.

The diatomaceous earth cake above is mixed vigorously with 1200 liters of acetone/water (90/10) for 4 hours. The mixture is filtered and the filtrate is concentrated to dryness in five equal portions. Each portion is triturated with basic methanol, concentrated and triturated with water as described above to afford a total of 288 grams of a crude preparation which is approximately one tenth as active as the preparation derived from the filtrate. This preparation is triturated thoroughly with 3 liters of dichloromethane-methanol (70/30, v/v) and the solution is concentrated to a small volume and is precipitated by addition of diethyl ether and hexane. Work up of the precipitate affords 51.2 grams of crude LL-014E605 complex. Each 5 gram sample of the crude LL-14E605 complex is dissolved and partitioned in 1 liter of the solvent mixture dichloromethane-methanol-water (50/20/30, v/v/v/). The lower phase of the mixture, containing most of the bioactivity, is worked up to afford 955 mg of partially purified LL-14E605 complex.

Example 5

Recovery of the LL-14E605 Complex via Solvent Extraction

The harvested fermentation mash (7100 liters) prepared as described in Example 2 is stirred with 70 liters of toluene. The mixture is filtered using a Ceraflo® Process System (Millipore). Further processing of the retentate (970 liters) is described in the next paragraph. The combined filtrate and diafiltrate (7300 liters) is passed through a Diaion ® HP-20 column (300-L) at 2–3 liter/minute. The column is eluted and the fractions are collected and assayed as described in Example 4. Fraction-22 (150 liters, 0.6% ammonium hydroxide in methanol eluate) containing most of the antibacterial activity is concentrated to a dark brown gum. The gum is partitioned in a mixture containing 4 liters of water, 2.7 liters of methanol and 6.7 liters of dichloromethane. The lower phase of the mixture is concentrated to a brown solid which is triturated with hexane, dried and is triturated with water to give 1.93 gram of partially purified LL-14E605 complex.

The retentate (970 liters) containing the mycelium from above is diluted with 800 liters of dichloromethane-methanol (50/50, v/v) and the mixture is filtered using a Ceraflo ® Process System via the constant volume wash mode; a total of 9000 liters of dichloromethane-methanol (50/50, v/v) is used. The filtrate (9140 liters) is concentrated to 1200 liters (methanol-water), 50/50, v/v) and mixed with 600 liters of methanol and 1200 liters of dichloromethane. The lower phase of the mixture is separated and the upper phase is mixed with 1240 liters of dichloromethane and 160 liters of methanol. The lower phase is combined with that separated previously (2000 liters total) and the mixture is concentrated to approximately 10 liters of brown lard-like material. This is triturated with 10 liters of water and the solids, collected by centrifugation, are triturated with 10 liters of hexane. The insolubles were collected by centrifugation re-suspended in water and freeze-dried to afford 468 gram of solids which is further purified by triturating with 55 L of hexane to afford 280 g of crude LL-14E605 complex.

Example 6

Purification of the LL-14E605 Complex by An Anion Exchange Adsorbent

The 33 grams of crude LL-14E605 complex prepared from the fermentation filtrate as described in Example 4 is further purified as the following. A 5-gram sample is dissolved in 50 ml of dichloromethane-methanol (50/50, v/v) and gravity loaded on a Sepralyte ® Primary/-Secondary Amine (Sepralyte ® PSA, Analytichem International, 40 μm) column (5 cm × 36 cm, 700 ml) packed in methanol and preconditioned with 4 bed-volumes each of 2% acetic acid in methanol and dichloromethane-methanol (50/50, v/v). Upon completion of loading, the column is eluted at 10 ml/minute with 900 ml of dichloromethane-methanol (50/50, v/v), 900 ml of methanol, and 3600 ml of 0.6% ammonium hydroxide in methanol. The dichloromethane-methanol (50/50, v/v) eluate containing good antibacterial activity, is concentrated to dryness, triturated with hexane and dried to yield 973 mg of partially purified LL-14E605 complex (preparation A). The methanol and the basic methanol eluate are collected into 20-ml fractions and the first 135 fractions containing most of the antibacterial activity are pooled, concentrated to dryness, triturated with hexane and dried to give 1.10 g of partially purified LL-14E605 complex (Preparation B).

Example 7

Preparation of LL-14E605β by Photolysis of Partially Purified LL-14E605 Complex A solution of the partially purified LL-14E605 complex, such as preparation B (889 mg) in Example 6, in 890 ml of methanol (containing 0.06% ammonium hydroxide)-dichloromethane (80/20, v/v) is divided evenly into two 3-L Fernbach flasks. The solutions in the flasks are stirred in the fume-hood, at room temperature, under fluorescent lamps. Aluminum foil is placed under the flasks to increase light intensity. The reaction mixture is analyzed by HPLC after 7 and 24 hours. The photo reaction is essentially complete after 7 hours. The reaction mixture is concentrated after 24 hours to afford 846 mg of crude LL-14E605β (8.3% pure) which can be further purified as described in Examples 8 and 9.

Example 8

Isolation of LL-14E605β by column Chromatography on a Polymeric Resin

A glass column (2.5 cm × 60 cm) packed with approximately 260 ml of Amberchrom ® CG-161M (50–100 μm, Toso Haas) in acetone is pre-conditioned at a flow rate of 10 ml/minute using the following gradient.

| Gradient Table for Pre-conditioning the Amberchrom ® Column | |
|---|---|
| Solvent mixture | Time |
| acetonitrile-buffer* (50/50, v/v) | 0 minute |
| acetonitrile-buffer* (50/50, v/v) | 30 minute |
| acetonitrile-buffer* (90/10, v/v) | 60 minute |
| acetonitrile-buffer* (90/10, v/v) | 120 minute |
| acetonitrile | 130 minute |
| acetonitrile | 145 minute |
| dichloromethane-methanol (50/50, v/v) | 155 minute |
| dichloromethane-methanol (50/50, v/v) | 245 minute |
| acetonitrile | 255 minute |
| acetonitrile | 285 minute |
| acetonitrile-buffer* (45/55, v/v) | 295 minute |
| acetonitrile-buffer* (45/55, V/v) | 385 minute |

*Buffer: 0.1 M trifluoroacetic acid, adjusted to pH 2.0 with concentrated ammonium hydroxide.

Amberchrom ® CG-161M (30 ml) is added to a solution of crude LL-14E605β (900 mg, 13% pure), such as the preparation A in Example 7 (or samples prepared in Example 8), in 50 ml of dichloromethane-methanol (70/30, v/v). The mixture is evaporated to dryness on a rotary evaporator. The LL-14E605 coated Amberchrom ® resin is suspended in the solvent mixture acetonitrile-buffer (45/55, v/v) and carefully layered on top of the preconditioned Amberchrom ® column. The column is eluted at 10 ml/minute using the following gradient.

| Gradient Table for Eluting the Amberchrom ® Column | |
|---|---|
| Solvent mixture | Time |
| acetonitrile-buffer* (45/55, v/v) | 0 minutes |
| acetonitrile-buffer* (45/55, v/v) | 120 minutes |
| acetonitrile-buffer* (90/10, v/v) | 130 minutes |
| acetonitrile-buffer* (90/10, v/v) | 160 minutes |
| acetonitrile | 170 minutes |
| acetonitrile | 150 minutes |
| dichloromethane-methanol (50/50, v/v) | 190 minutes |
| dichloromethane-methanol (50/50, v/v) | 220 minutes |

*Buffer: 0.1 M trifluoroacetic acid, adjusted to pH 2.0 with concentrated ammonium hydroxide.

Fractions (20 ml each) collected through the elution are analyzed by HPLC and antimicrobial assay. Fractions containing primarily LL-14E605β (fractions 32–40) are pooled, concentrated to remove acetonitrile, neutralized and desalted over an Amberchrom ®CG-161M column (1.5 cm × 25 cm). Partially purified LL- 14E605β (80 mg, 70% pure) is recovered from Amberchrom® by eluting with dichloromethane-methanol (50/50, v/v). Alternatively, the desalting can be accomplished by partitioning the antibiotic into the lower phase of the solvent system dichloromethane-methanol-water (5/2/3, v/v/v).

Example 9

Purification of LL-14E605β by Centrifugal Partition Chromatography

Final purification of LL-14E605β is accomplished by Centrifugal Partition Chromatography (CPC) Model LLN (Sanki Laboratories, Inc.) equipped with 6 Type 250W cartridges (125 ml total volume). A partially purified sample of LL-14E605β (120 mg, 39% pure) is dissolved in 7.5 ml each of the upper and lower phases of the solvent system, toluene-dichloromethane-methanol-buffer (0.1M trifluoroacetic acid, adjusted to pH 2.0 with concentrated ammonium hydroxide), 108/792/700/400 (v/v/v/v) and is loaded on the CPC instrument which is filled with the lower phase of the same solvent system. The separation is carried out in the ascending mode with the upper phase of the solvent system as the mobile phase at 0.75 ml/minute, 800 rpm, and fractions are collected every 4 minutes. Fractions 26–33 containing pure LL-14E605β based on HPLC analysis are pooled, concentrated to dryness, and is partitioned in 100 ml of dichloromethane-methanolwater (5:2:3). The lower phase is concentrated to afford 54.5 mg of 63% pure LL-14E605 containing ammonium trifluoroacetate.

Example 10

Purification of LL-14E605 Complex by using a Polymeric Adsorbent

Crude 14E605 complex (30 g) such as prepared in Example 5 is stirred in 300 ml of methanol containing 1% of formic acid until the insolubles become a fine suspension. The insolubles are separated by centrifugation and the solution is diluted with 1200 ml of water and neutralized with ammonium hydroxide. The cloudy mixture is loaded (10 ml/min) onto a preconditioned Diaion® HP-20 column (5 cm×45 cm, 900 ml) equilibrated in water. The column is then washed with 2700 ml of water and eluted (10 ml/min) sequentially with 1) a linear gradient of water to methanol over 900 ml, 2) 900 ml of methanol, 3) a linear gradient of methanol to dichloromethane-methanol (50:50). The fractions collected at regular intervals are analyzed by antimicrobial assay and most of the bioactivity is concentrated in the dichloromethane-methanol (50:50) eluate which is concentrated and freeze dried to yield 4.58 g of partially purified LL-14E605 complex.

Example 11

Alternative Photolysis Procedure for the Preparation of LL-14E605β from Partially Purified LL-14E605 Complex A solution of partially purified LL-14E605 complex (2.0 g, such as prepared in Example 10) in 2000 ml of methanol containing 0.6% ammonium hydroxide-dichloromethane (80:20), in a 3.5-L Pyrex beaker equipped with a magnetic stir is photolyzed in a Rayonet Photochemical Reactor (Southern N.E. Ultraviolet Co.) using ten 350 nm 12″ fluorescent tubes. Samples are taken at regular intervals to monitor the progress of the reaction by HPLC analysis. The maximum yield of LL-14E605 is achieved after 5 minutes of photolysis.

Example 12

Purification of LL-14E605β by Centrifugal Partition Chromatography

A photolysis mixture which is enriched in LL-14E605β dryness and redissolved in 18 ml of the lower phase and 10 ml of the upper phase of the solvent system, toluene-dichloromethane-methanol-buffer (0.1M trifluoroacetic acid, adjusted to pH 2.0 with concentrated ammonium hydroxide), 108/792/700/400 (V/V/V/V). The antibiotic solution is loaded on the same CPC instrument as described in Example 9 equipped with 6 Type 1000E cartridges (425 ml total volume) which is filled with the stationary (lower) phase and equilibrated with the mobile (upper) phase (35 ml stationary phase displacement) of the same solvent system. The separation is carried out in the ascending mode (Example 9) at 23° C., 4 ml/min, 700 rpm, and fractions are collected every 4 minutes. Fractions 56–84 containing LL-14E605β based on HPLC analysis are combined, neutralized, concentrated to dryness and desalted by the triturating the solids twice with 20 ml of water to give 183 mg partially purified LL-14E605β (24% pure).

The partially purified LL-14E605β sample above is redissolved in 7.5 ml each of the lower and upper phase of the same solvent system above and rechromatographed on the same CPC instrument under identical conditions to afford 94.3 mg of 45% pure LL-14E605β from fractions 26–50.

Example 13

Purification of LL-14E605β by Centrifugal Partition Chromatography

A photolysis mixture which is enriched in LL-14E605 prepared in the same manner as described in Example 11 is concentrated to dryness (1.2 g) and redissolved in 15 ml of the lower phase and 15 ml of the upper phase of the solvent system as described in Example 12. The sample is loaded onto the CPC instrument which is previously filled with lower phase and equilibrated with mobile phase flowing at 4 ml per minute. The instrument is the same as described in Example 12, but with the following changes. The solvent delivery pump is replaced with a Waters Model 590 Programmable Solvent Delivery Module, the two rotary valves are replaced with two Rheodyne low pressure Teflon valves, Model 5042 (1.5 mm bore, 4-way rotary), a third Rheodyne Model 5042 valve is added to enable the flow through the sample loop to be reversed. The separation is carried out in the ascending mode (Example 9) at 23° C., 4 ml/min, 700 rpm, and fractions are collected every 4 minutes. Fractions 30–40 are neutralized with aqueous NH₄OH, concentrated to dryness then desalted by triturating the solids in 20 ml H₂O to give 75.8 mg of partially pure LL-14E605β (34% pure).

Example 14

Purification of LL-14E605β by Centrifugal Partition Chromatography

A photolysis mixture which is enriched in LL-14E605β prepared in the same manner as described in Example 9 is concentrated to dryness (0.20 g) and redissolved in 3 ml of the lower phase and 3 ml of the upper phase of the solvent system as described in Example 12. The sample is loaded onto the CPC instrument which is filled with lower phase and equilibrated with mobile phase flowing at 1 ml per minute. The instrument is the same as described in Example 13, but equipped with 6 Type 250W cartridges (125 ml total volume). The separation is carried out in the ascending mode (Example 9) at 23° C., 1 ml/min., 400 rpm and fractions are collected every 4 minutes. Fractions 25–38 are combined, neutralized with aqueous NH4OH, concentrated, redissolved in 50 ml of water and loaded onto the instrument using a solvent system of 60 ml of water, 110 ml of methanol and 400 ml of methanol-dichloromethane-toluene (1:1:1). Fractions (10 ml each) are collected starting with the last 100 ml of water. Fractions 23–33 (methanol-dichloromethane-toluene) are combined and concentrated to dryness to yield 21.8 mg of pure LL-14E605β. The UV, IR, CD, $^1$HNMR and $^{13}$CNMR spectra of this sample is shown in FIGS. I–V.

Example 15

Preparation and Purification of O-Methyl-LL-14E605beta

Two samples of the 45% pure LL-14E605β such as prepared in Example 12 are combined and dissolved in 10 ml of dichloromethane-methanol (80:20), treated with excess freshly prepared diazomethane in diethylether. Methanol is added to the reaction mixture as necessary to keep the antibiotic in solution. Upon decomposing the excess diazomethane, the reaction mixture is concentrated to dryness and the residue is redissolved in 8 ml each of the upper and lower phase of the solvent system, toluene-dichloromethane-methanol buffer (0.1M trifluoroacetic acid, adjusted to pH 2.0 with concentrated ammonium hydroxide), 108/792/700/400 (v/v/v/v) and chromatographed on the CPC instrument equipped with 6 Type 1000E cartridges in the ascending mode (Example 12) at 23° C., 5 ml/min., 700 rpm, and 10 ml/fraction. Fractions 56–84 containing o-methyl-LL-14E605β are neutralized, concentrated to dryness, desalted by triturating three times with 20 ml of water, freeze dried, and triturated with hexane to give 45.6 g of 87% pure o-methyl-LL-14E605β. The purity is estimated based on % of total area under the peaks in the HPLC chromatogram (UV detection at 250 nm). The UV, IR, CD, $^1$HNMR and $^{13}$CNMR spectra of this sample is shown in FIGS. VI–X.

What is claimed is:

1. The isolated and substantially pure form of compound LL-14E605β which has the structure:

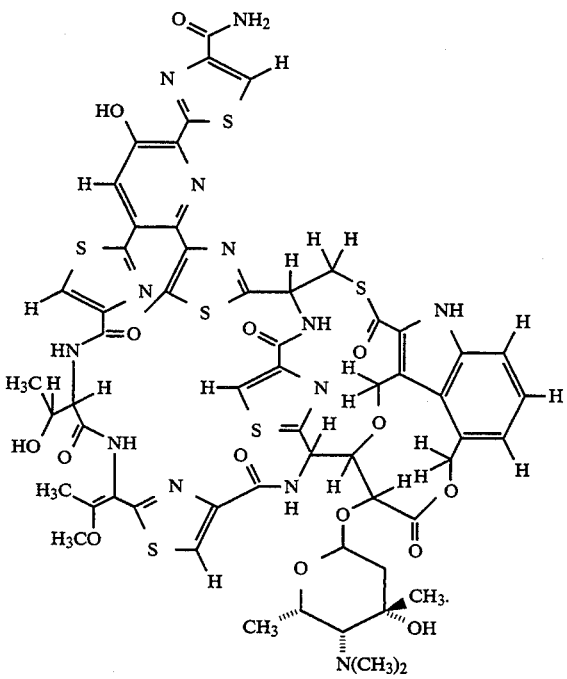

2. The isolated and substantially pure form of compound O-Methyl-LL-14E605β which has the structure:

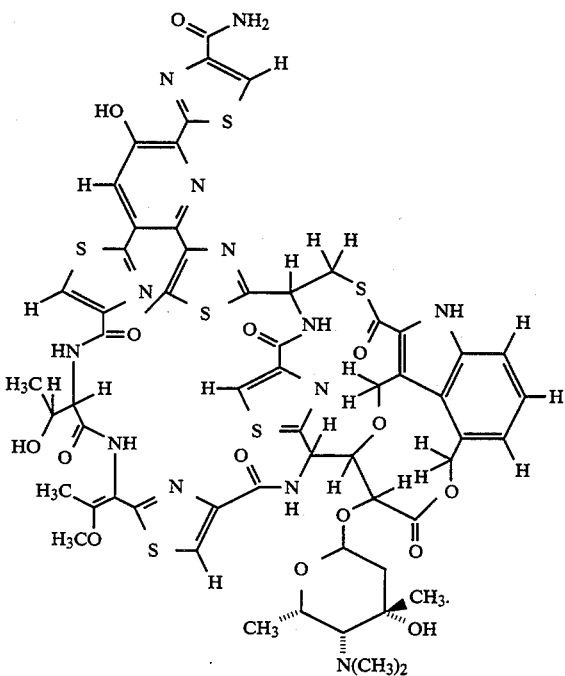

3. A method of treating bacterial infections in warm-blooded animals which comprises administering to said animals an antibacterially effective amount of antibiotic LL-14E605β as defined in claim 1.

4. A method of treating bacterial infections in warm-blooded animals which comprises administering to said animals an antibacterially effective amount of antibiotic O-methyl-LL-14E605β as defined in claim 2.

* * * * *

UNITED STATES PATENT AND TRADEMARK OFFICE
CERTIFICATE OF CORRECTION

PATENT NO. : 5,451,581
DATED : September 19, 1995
INVENTOR(S) : May D. Lee, et al Page 1 of 2

It is certified that error appears in the above-indentified patent and that said Letters Patent is hereby corrected as shown below:

In claim 2, column 16, lines 31 to 58 delete the structure :

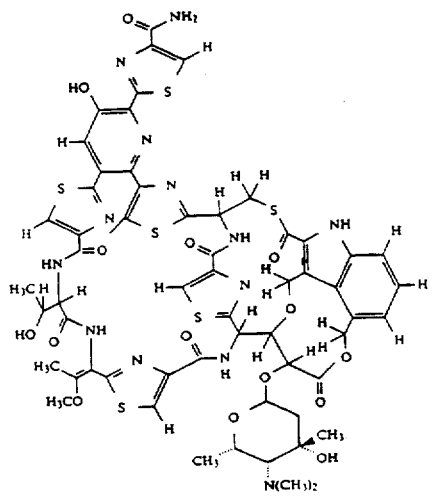

UNITED STATES PATENT AND TRADEMARK OFFICE
CERTIFICATE OF CORRECTION

PATENT NO. : 5,451,581
DATED : September 19, 1995
INVENTOR(S) : May D. Lee, et al.

It is certified that error appears in the above-indentified patent and that said Letters Patent is hereby corrected as shown below:

insert the following structure:

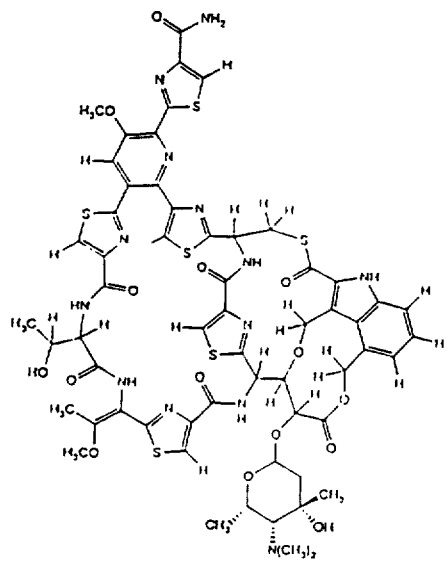

Signed and Sealed this

Nineteenth Day of December, 1995

*Attest:*

BRUCE LEHMAN

*Attesting Officer*      Commissioner of Patents and Trademarks